United States Patent
Chevreux

(10) Patent No.: US 11,254,920 B2
(45) Date of Patent: *Feb. 22, 2022

(54) FACTOR VII COMPOSITION HAVING A SUBSTANTIALLY HOMOGENOUS ISOELECTRIC POINT

(71) Applicant: Laboratoire Francais du Fractionnement et des Biotechnologies, Les Ulis (FR)

(72) Inventor: Guillaume Chevreux, Paris (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/868,803

(22) Filed: May 7, 2020

(65) Prior Publication Data

US 2020/0270596 A1 Aug. 27, 2020

Related U.S. Application Data

(62) Division of application No. 14/896,763, filed as application No. PCT/EP2014/062051 on Jun. 10, 2014, now Pat. No. 10,683,492.

(30) Foreign Application Priority Data

Jun. 11, 2013 (FR) ..................... 13/55403

(51) Int. Cl.
| | |
|---|---|
| *A61K 35/14* | (2015.01) |
| *A61K 38/48* | (2006.01) |
| *C07K 1/00* | (2006.01) |
| *C07K 16/00* | (2006.01) |
| *C07K 17/00* | (2006.01) |
| *A61K 38/43* | (2006.01) |
| *A61K 38/57* | (2006.01) |
| *C07K 14/745* | (2006.01) |
| *A61K 38/36* | (2006.01) |
| *A61P 7/02* | (2006.01) |
| *A61K 38/00* | (2006.01) |
| *A61P 7/00* | (2006.01) |
| *C12N 9/64* | (2006.01) |
| *A01K 67/027* | (2006.01) |

(52) U.S. Cl.
CPC ........ *C12N 9/6437* (2013.01); *A01K 67/0275* (2013.01); *A01K 67/0276* (2013.01); *A61K 38/36* (2013.01); *A61P 7/00* (2018.01); *C07K 14/745* (2013.01); *A01K 2217/052* (2013.01); *A01K 2227/107* (2013.01); *A01K 2267/02* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,784,950 | A | 11/1988 | Hagen et al. |
| 5,997,864 | A | 12/1999 | Hart et al. |
| 6,903,069 | B2 | 6/2005 | Pingel et al. |
| 10,344,272 | B2 | 7/2019 | Chtourou et al. |
| 10,364,425 | B2 | 7/2019 | Chtourou et al. |
| 2006/0179500 | A1 | 8/2006 | Meade et al. |
| 2009/0311239 | A1 | 12/2009 | Chtourou et al. |
| 2020/0362329 | A1* | 11/2020 | Chevreux ............ C07K 14/745 |

FOREIGN PATENT DOCUMENTS

| | | |
|---|---|---|
| CN | 101460189 A | 6/2009 |
| EP | 0527063 A1 | 2/1993 |
| EP | 2037955 A2 | 3/2009 |
| EP | 2687595 A1 | 1/2014 |
| FR | 2901707 A1 | 12/2007 |
| WO | 2007138199 A3 | 1/2008 |
| WO | 2008099077 A3 | 5/2009 |
| WO | 2010149907 A1 | 12/2010 |

OTHER PUBLICATIONS

English language machine translation of Bardat et al. WO Publication No. 2010/149907 A1 published on Dec. 29, 2010 (accessed on Sep. 9, 2021) (Year: 2021).*
Bigge et al., "Nonselective and Efficient Fluorescent Labeling of Glycans Using 2-Amino Benzamide and Anthranilic Acid," Analytical Biochemistry, vol. 230, 1995, pp. 229-238.
Chevreux et al., "N-/O-glycosylatlon analysis of human FVIIa produced in the milk of transgenic rabbits," Glycobiology, vol. 23, No. 12, 2013, pp. 1531-1546.
Echelard et al., "Transgenic Technology: a Validated Approach for Large-Scale Manufacturing," vol. 14, 2009, No. 40, pp. 50-54.
Fenaille et al., "Mass spectrometric characterization of N- and O-glycans of plasma-derived coagulation factor VII," Gylconoj J., vol. 24, 2008, pp. 827-842.
Graham et al., "Characteristics of a Human Cell Line Transformed by DNA from Human Adenovirus Type 5," J. Gen. Virol., vol. 36, 1977, pp. 59-72.
GTC Biotherapeutics Reports Third Quarter 2007 Financial Results, Nov. 1, 2007, accessed from: http://www.wikinvest.com/stock/GTC_Biotherapeutics_(GTCB)/.
Guile et al., "A Rapid High-Resolution High-Performance Liquid Chromatographic Method for Separating Glycans Mixtures and Analyzing Oligosaccharide Profiles" Analytical Biochemistry, vol. 240, 1996, pp. 210-226.

(Continued)

*Primary Examiner* — Thea D'Ambrosio
(74) *Attorney, Agent, or Firm* — Rouget F. Henschel; Potomac Law Group, PLLC

(57) ABSTRACT

The present invention relates to a factor VII composition having a substantially homogeneous isoelectric point and to a method for formulating such a composition. The present invention also relates to the therapeutic use of a factor VII composition having a substantially homogeneous isoelectric point.

10 Claims, 6 Drawing Sheets

(56) References Cited

OTHER PUBLICATIONS

Figure 1:
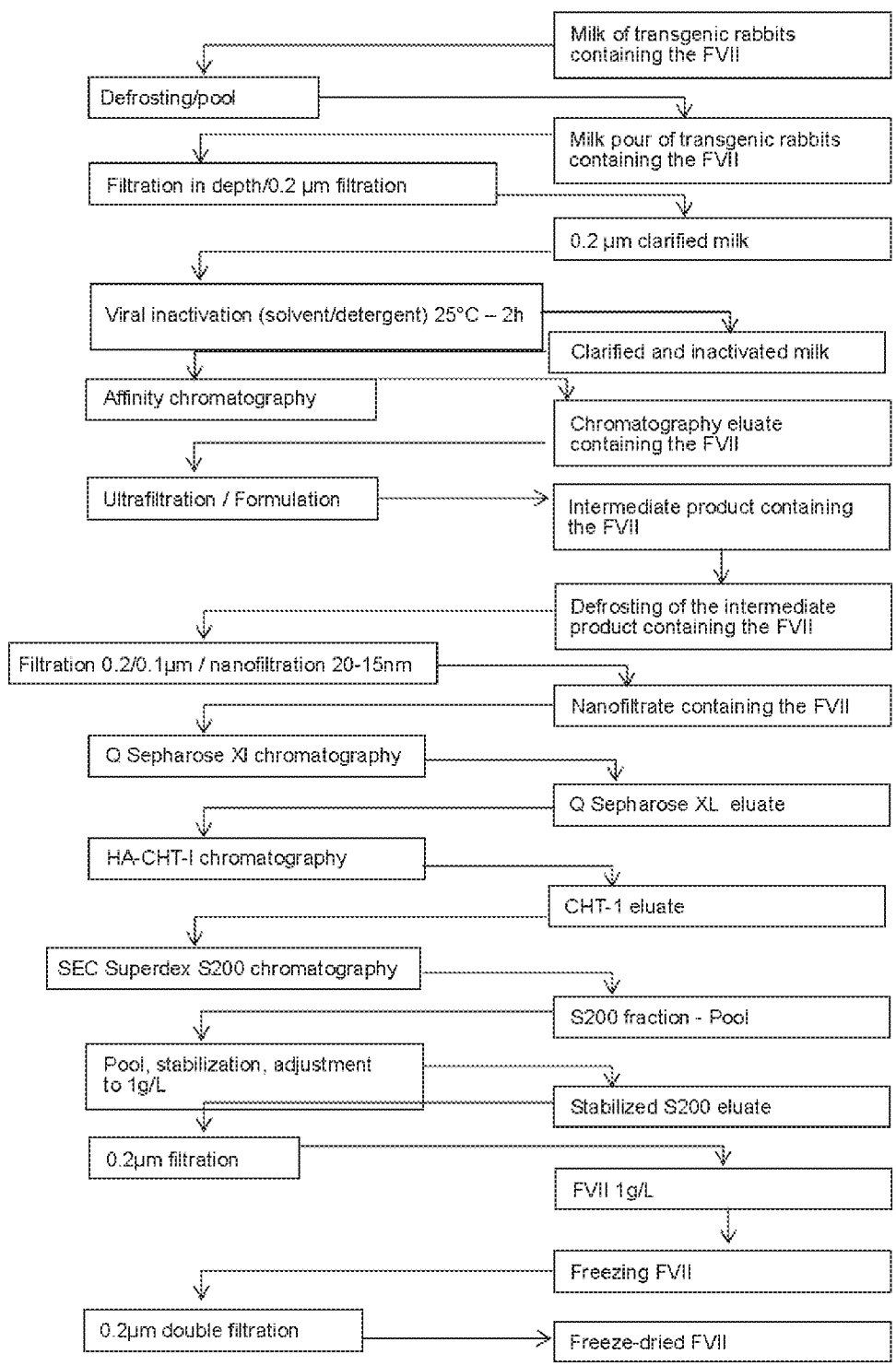

Hermentin et al., "The hypothetical N-glycan charge: a number that characterizes protein glycosylation," Glycobiology, vol. 6, No. 2, 1996, pp. 217-230.

International Search Report and Translation of the Written of the International Searching Authority issued in corresponding application No. PCT/EP2014/062051 dated Jan. 8, 2014.

Jurlander et al., "Recombinant Activated Factor VII (rFVIIa): Characterization, Manufacturing, and Clinical Development," Seminars in Thrombosis and Hemostasis, vol. 27, No. 4, 2001, pp. 373-384.

Klausen et al., "Analysis of the Site-Specific Asparagine-Linked Glycosylation of Recombinant Human Coagulation Factor VIIa by Glycosidase Digestions, Liquid Chromatography, and Mass Spectrometry" Molecular Biotechnology, vol. 9, 1998, pp. 195-204.

Kornfeld et al., "Assembly of Asparagine-Linked Oligosaccharides," Annual Review of Biochemistry, vol. 54, 1985, pp. 631-664.

Maksimenko et al., "Use of Transgenic Animals in Biotechnology: Prospects and Problems," Acta Naturae, vol. 5, No. 1, 2013, pp. 33-46.

Persson et al., "Ca2+ Binding to the First Epidermal Growth Factor-like Domain of Factor VIIa Increases Amidolytic Activity and Tissue Factor Affinity", The Journal of Biological Chemistry, vol. 272, No. 32, Aug. 1997, pp. 19919-19924.

Persson, "Characterization of the interaction between the light chain of factor VIIa and tissue factor," FEBS Letters, vol. 413, 1997, pp. 359-363.

Thim et al., "Amino Acid Sequence and Posttranslational Modifications of Human Factor VIIa from Plasma and Transfected Baby Hamster Kidney Cell", Biochemistry, vol. 27, 1998, pp. 7785-7793.

Urlaub et al., "Isolation of Chinese hamster cell mutants deficient in dihydrofolate reductase activity," Proc. Natl. Acad. Sci., vol. 77, No. 7, Jul. 1980, pp. 4216-4220.

Waechter et al., "Effect of methylation on expression of microinjected genes," Proc. Natl. Acad. Sci., vol. 79, Feb. 1982, pp. 1106-1110.

Wang et al., "Lyophilization and development of solid protein pharmaceuticals," International Journal of Pharmaceutics, vol. 203, 2000, pp. 1-60.

Yates et al., "Proteomics by Mass Spectrometry: Approaches, Advances, and Applications," Annual Review of Biomedical Engineering., vol. 11, 2009, pp. 49-79.

* cited by examiner

FACTOR VII COMPOSITION HAVING A SUBSTANTIALLY HOMOGENOUS ISOELECTRIC POINT

This application is a divisional of U.S. application Ser. No. 14/896,763, filed Dec. 8, 2015, which is a U.S. National Stage of PCT/EP2014/062051, filed Jun. 10, 2014, which claims priority to French Patent Application No. 13/55403, filed Jun. 11, 2013, all of which are hereby incorporated by reference in their entirety.

TECHNICAL FIELD

The present invention relates to a factor VII composition having a substantially homogeneous isoelectric point and to a method for formulating such a composition. The present invention also relates to the therapeutic use of a factor VII composition having a substantially homogeneous isoelectric point.

TECHNOLOGICAL BACKGROUND

The Factor VII (FVII) is a glycoprotein depending on vitamin K, which is involved in the extrinsic route of blood coagulation. In its activated form (FVIIa), the factor VIIa is involved in the coagulation process by forming a complex with the tissue factor (TF) and by activating the factor X and the factor IX into factor Xa and IXa, respectively. So FVIIa has the capability of triggering coagulation of blood when the cascade of reactions leading to blood coagulation is interrupted or deficient, for example in the absence of factor VII or IX. This is why the factor VIIa has been used for a long time as a drug for treating certain disorders of blood coagulation expressed by bleeding, and notably for treating patients having factor VIII deficiency (hemophilia of type A) or factor IX deficiency (hemophilia of type B) and having inhibitors against these factors, for treating patients having congenital factor VII deficiency, or as a product for preventing hemorrhages which may occur during surgical operations.

The factor VII is secreted in the form of a single peptide chain of 406 amino acids, with a molecular weight of about 50 kDa, which is cut at the $Arg_{152}$-$Ile_{153}$ (Arginine 152-Isoleucine 153) bond during its activation into FVIIa. The Factor VIIa resulting from this therefore consists of a light chain of 152 amino acids, with a molecular weight of about 20 kDa. and of a heavy chain of 254 amino acids, with a molecular weight of about 30 kDa, bound together through a single disulfide bridge ($Cys_{135}$-$Cys_{262}$).

Four distinct structural domains may be identified in the sequence of the factor VII: an N-terminal γ-carboxylic domain (Gla domain), two "epidermal growth factor (EGF)-like": domains as well as a serine protease domain.

The plasma Factor VIIa moreover includes several post-translational modifications among which: γ-carboxylation of the first ten glutamic acids of its sequence, partial hydroxylation of the aspartic acid 63, O-glycosylation of the serines 52 and 60 ($Ser_{52}$ and $Ser_{60}$) and N-glycosylation of the asparagines 145 and 322 ($Asn_{145}$ and $Asn_{322}$) (Fenaille F. et al., Mass spectrometric characterization of N- and O-glycans of plasma-derived coagulation factor VII. Glycoconj. J. 25.9 (2008): 827-42).

The biological activity of the factor VII thus strongly depends on the nature and on the proportion of the oligosaccharide structures which are attached to the protein, and which may affect many aspects of the therapeutic efficiency such as for example, solubility, resistance to proteolytic attacks, thermal inactivation, immunogenicity, half-life, bioactivity, bioavailability and stability of the factor VII.

It appears that these post-translational modifications, which often vary from one plasma factor VII molecule to another, lead to some heterogeneity of the molecules present in the pharmaceutical compositions of factor VII. Such heterogeneity notably has the drawback of complicating the steps for formulating the factor VII with view to the preparation of pharmaceutical compositions intended for treating patients. Indeed, it is frequent that a significant proportion of the purified factor VII molecules precipitate during the formulation step: the result of this is a loss of active raw material, as well as the presence of the factor VII having become inactive into pharmaceutical compositions intended for therapeutic treatment.

Because of the numerous drawbacks of the use of human plasma (risks of viral contamination, difficulty in purification, supply . . . ) as a source of pharmaceutical products, it is now preferred to produce the factor VII in recombinant or transgenic systems. However, insofar that glycosylation is a complex post-translational modification which directly depends on the cell system used, large scale production of proteins in heterologous cells often leads to the production of polypeptides having an identical primary structure, but having variable oligosaccharide structures.

For example, this is the case of NovoSeven®, a drug which has been authorized on the European market since 1996 and authorized on the American market in 1999, produced by the Danish firm NovoNordisk, the active ingredient of which is eptacog alfa (human recombinant activated coagulation Factor VII produced by genetic engineering from BKH kidney cells of newborn hamsters).

This is also the case, of recombinant transgenic FVII described in application EP 2 037 955 A, filed on May 31, 2007 by LFB Biotechnologies.

It thus appears that for these recombinant factors VII, the heterogeneity of the post-translational modifications borne by the molecules of Factor VII perturb the formulation step and contribute to reducing the stability and/or the specific activity of the final pharmaceutical products, by promoting the presence of precipitated factor VII molecules. The result of this is many difficulties for managing to prepare pharmaceutically acceptable compositions having a uniform and predetermined clinical efficiency.

Therefore there exists an increasing need for factor VII compositions having improved chemical and physical stability at room temperature and capable of facilitating and improving the yield of the formulation steps aiming at preparing pharmaceutical compositions intended for the treatment of patients affected by hemophilia with inhibitors or congenital factor VII deficiency.

SUMMARY OF THE INVENTION

The applicant has surprisingly discovered that factor VII compositions, for which the factor VII molecules have a substantially homogeneous isoelectric point facilitate the formulation step at an optimum pH, preferably at an optimum pH of 6.0±0.2, of pharmaceutical compositions while avoiding precipitation of the factor VII.

The present invention therefore relates to a factor VII composition in which the factor VII molecules have a substantially homogeneous isoelectric point.

In a particular embodiment, the present invention relates to a factor VII composition in which, among all the N-glycan forms of the factor VII of the composition, at least 60% of said N-glycan forms are monocharged and among all the factor VII molecules of the composition, at least 80% of said molecules have γ-carboxylation on 9 residues of glutamic acid.

In a particular embodiment, at least 65%, preferably at least 70% or preferably at least 80% of the N-glycan forms of the factor VII of the composition are monocharged.

In a particular embodiment, at least 85%, preferably from 85% to 100% or preferably from 90% to 100%, or preferably from 95% to 100% of the factor VII molecules of the composition have γ-carboxylation on 9 residues of glutamic acid.

In a particular embodiment, the γ-carboxylation level of the factor VII composition of the invention on the residue of glutamic acid 35 ($Glu_{35}$ relatively to the sequence of the plasma factor VII) is less than 20%, or preferably less than 15%, or still preferably less than 10%, preferably less than 5%.

In a particular embodiment, the present invention relates to a factor VII composition, for which at least 60% of the N-glycan forms of the factor VII of the composition are monosialylated complexes.

In a particular embodiment, at least 10%, preferably at least 15%, or preferably at least 20%, or preferably at least 25% of the N-glycan forms of the factor VII of the composition are high Mannose/hybrids.

In a particular embodiment at least 90%, preferably at least 95% of the factor VII molecules of the composition have an isoelectric point comprised in a pH unit interval of less than 1.2.

In a particular embodiment, at least 50/o %, or preferably at least 55% or preferably 60% of the factor VII molecules of the composition have an isoelectric point comprised within a pH unit interval of less than 1; preferably less than 0.5; or preferably less than 0.4.

In another particular embodiment, the factor VII of the invention is a recombinant or transgenic factor VII. Preferably, the factor VII of the composition is produced by transgenic rabbits. In an embodiment, the factor VII of the composition is an activated factor VII.

Another object of the invention relates to the use of the factor VII composition for the treatment of bleeding episodes and for preventing hemorrhages occurring during surgical operations or invasive procedures in the groups of the following patients:

in patients affected with congenital hemophilia with inhibitors directed against the coagulation factors VIII or IX (hemophilia A or B), in patients affected with congenital hemophilia in which a strong anamnestic response to the administration of factor VIII or of factor IX is predictable.

in patients affected with acquired hemophilia, and/or in patients having a congenital FVII deficiency.

Another object of the invention concerns a method for obtaining a factor VII composition according to the invention comprising the steps of:

(a) inserting a DNA sequence comprising a gene encoding for factor VII in an embryonic non-human mammal, said gene being under the transcriptional control of the beta-casein promoter, (b) transferring the embryos obtained in step a) into the oviduct of a female non-human mammal so that it develops into an adult mammal, (c) inducing lactation in the adult non-human mammal obtained in step b) of the female type or in a female descendant of the non-human mammal wherein the gene and the promoter are present in its genome, (d) collecting milk of said non-human mammal, and (e) purifying the factor VII present in the milk collected.

Another object of the invention relates to a method for formulating a factor VII composition comprising the mixing of the factor VII composition according to the invention with a buffer solution, pH adjustment if required, filtration and then drying if necessary in order to obtain the solid form.

Other features and advantages of the present invention will become apparent upon reading the detailed description which follows and of the preferred embodiment of the invention, given as an example and with reference to appended figures.

CAPTION OF THE FIGURES

FIG. 1: Method for purifying and extracting the factor VII of the invention.

Figure 2:
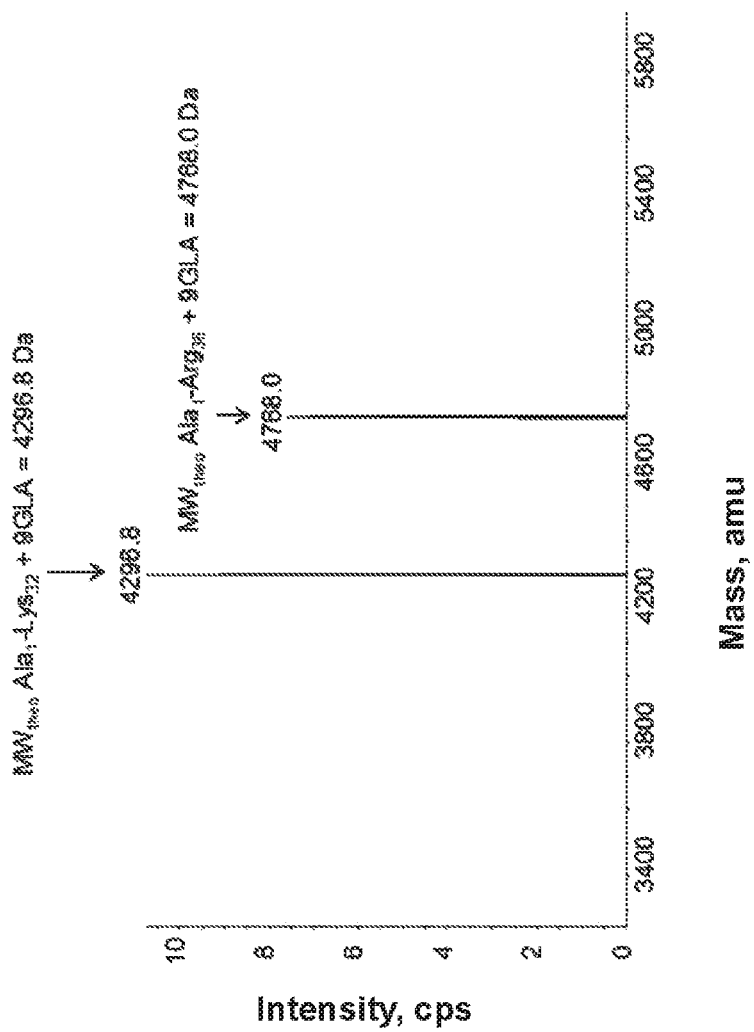

FIG. 2: Mass spectrum of the N-terminal peptides [$Ala_1$-$Arg_{36}$] and [$Ala_1$-$Lys_{32}$] of the factor VII of the invention.

Figure 3:
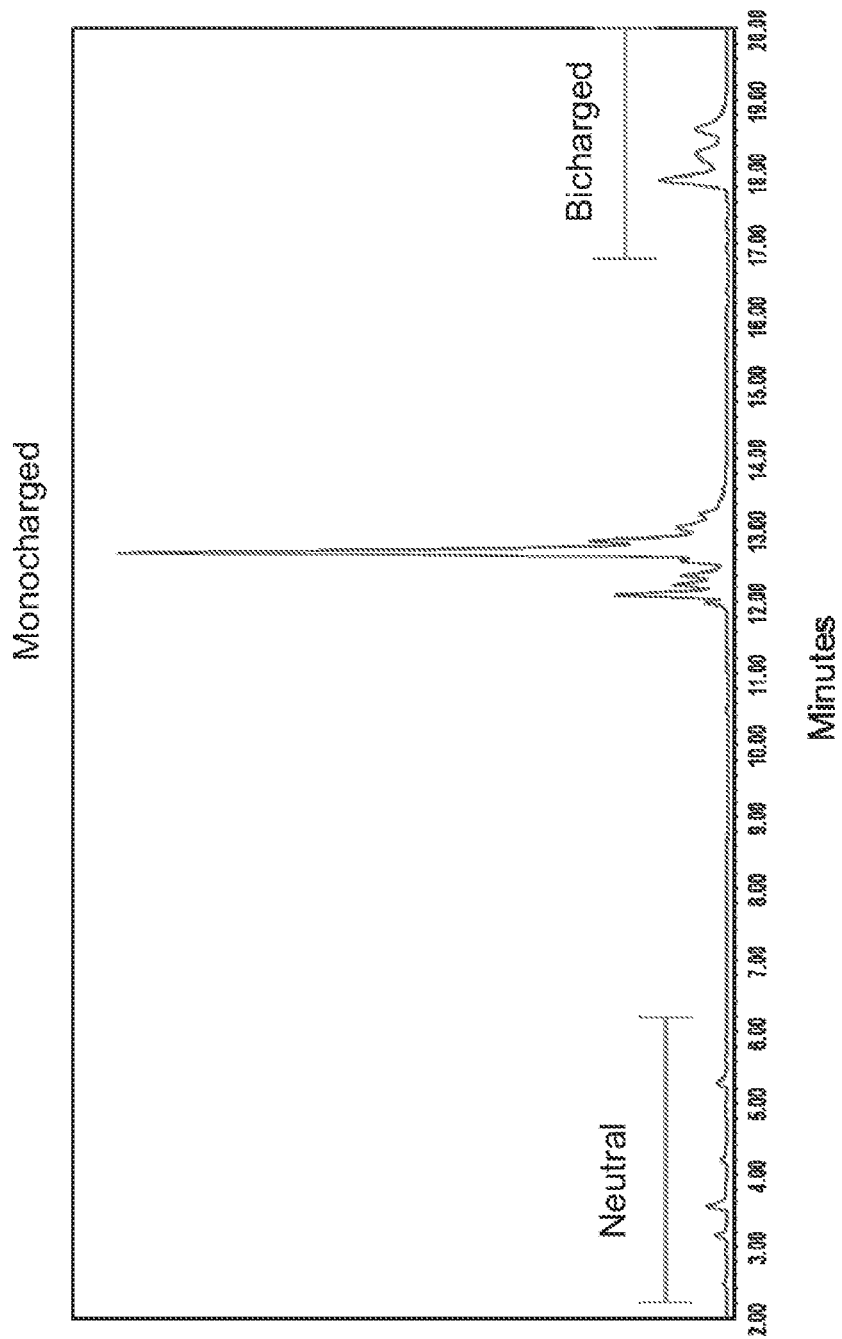

FIG. 3: Charge profiling of the N-glycan forms of the factor VII of the invention obtained by ultra-high performance liquid chromatography having an anion exchanger resin coupled with detection by fluorescence («AEX-UPLC/FD»)

Figure 4:
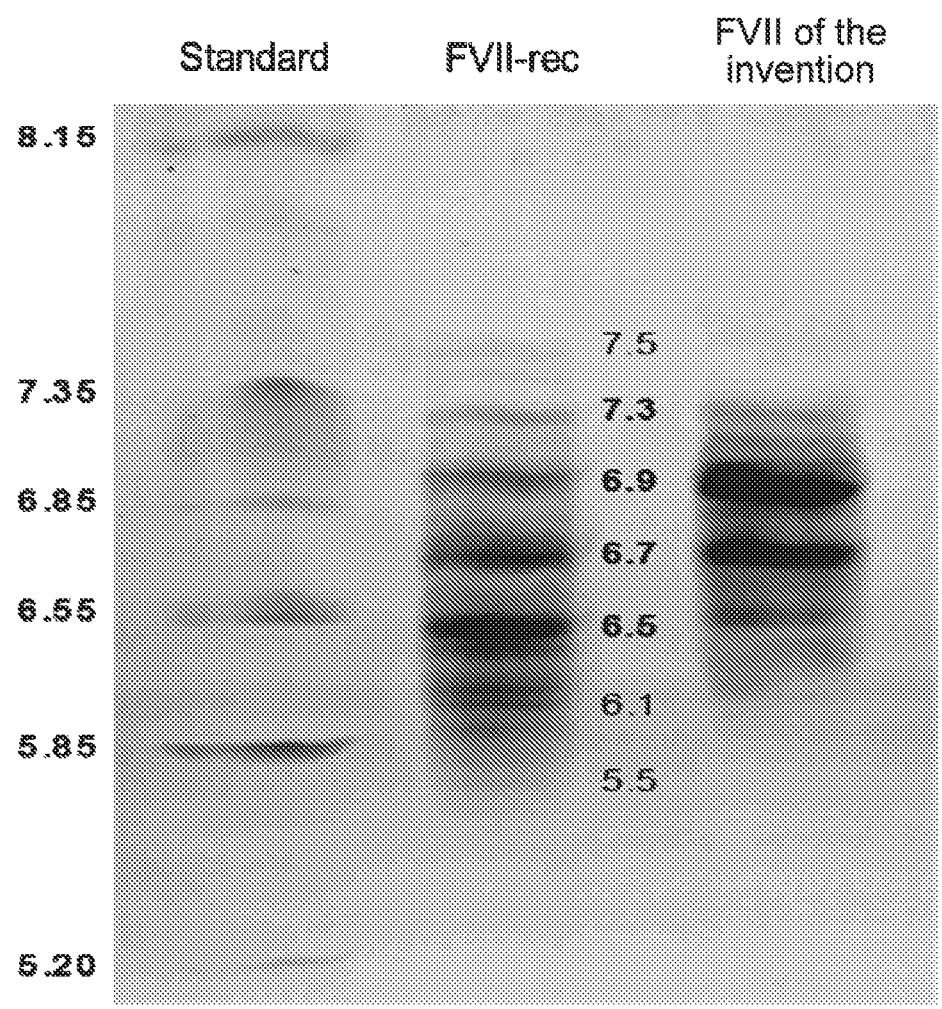

FIG. 4: Comparison of the isoelectric points of the factor VII of the invention and of a recombinant factor VII (Novoseven®) obtained by the isoelectric focusing method («IEF»).

Figure 5:
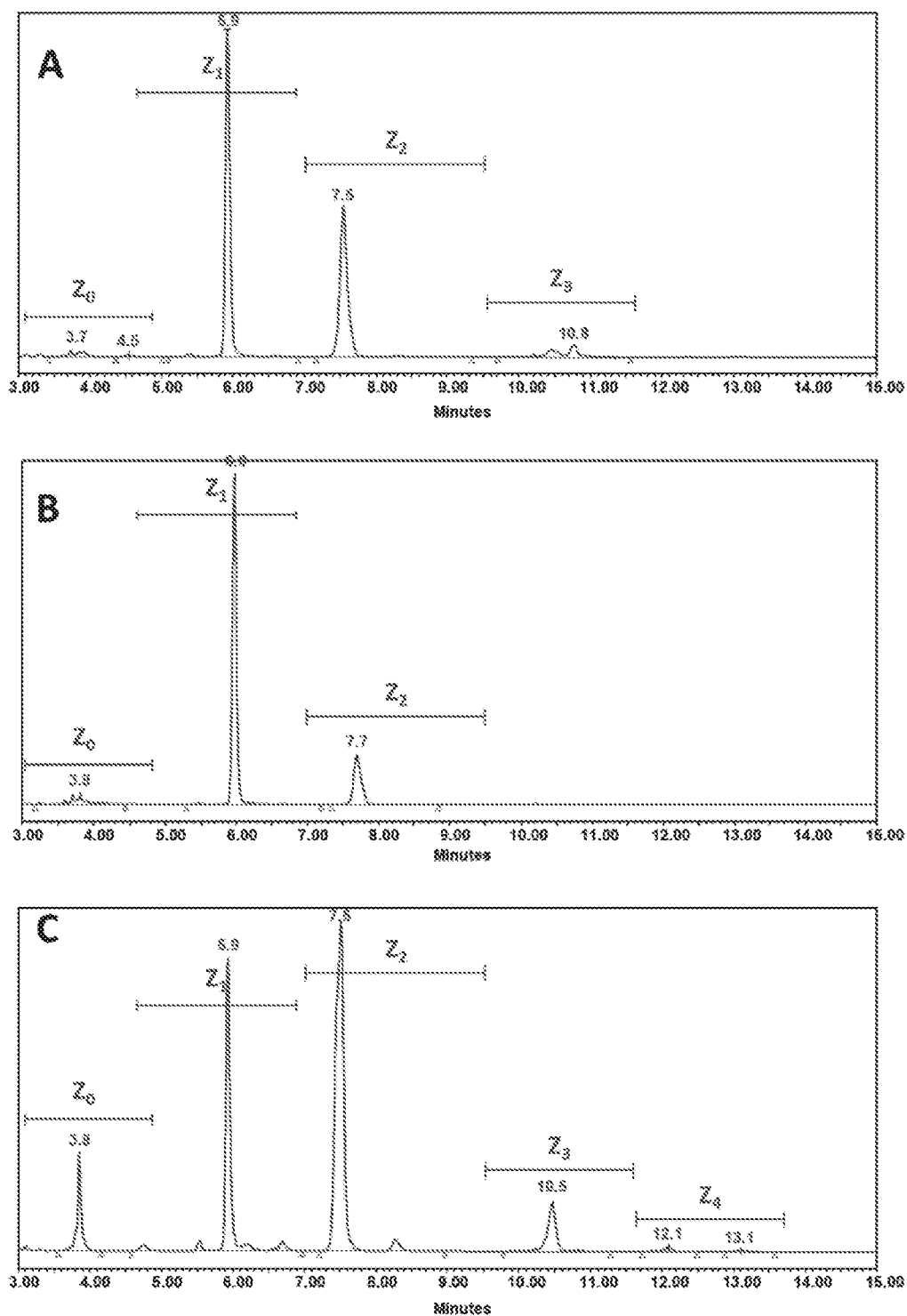

FIG. 5: Profiling of charge of N-glycan forms of Factor VII of the invention, of Factor VII from WO2007/138199 and a recombinant Factor VII (Novoseven®) obtained by ultra high performance liquid chromatography having an anion exchange resin coupled to detection by fluorescence ("AEX-UPLC/FD")

Figure 6:
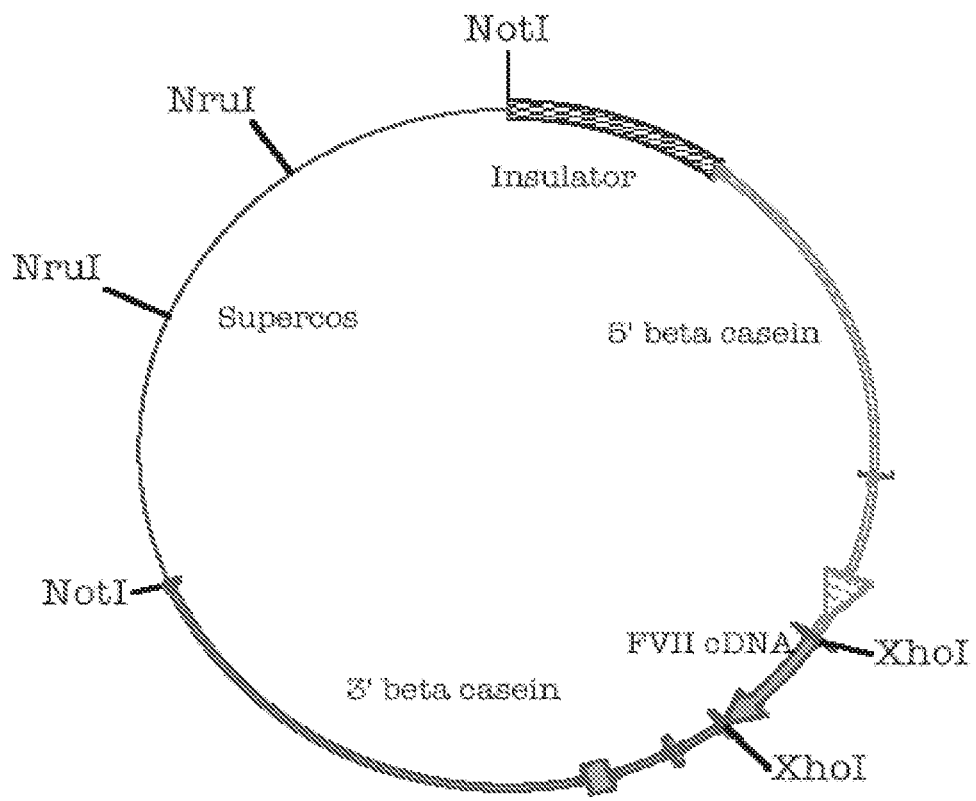

FIG. 6: Expression vector used for the generation of non-human mammals expressing human recombinant FVII according to the invention.

DETAILED DESCRIPTION

The factor VII composition chemically and physically stable at room temperature and easy to formulate according to the present invention is characterized in that the factor VII molecules which make it up, have a substantially homogeneous isoelectric point.

Advantageously, the factor VII composition according to the invention comprises factor VII molecules, in which the factor VII molecules have a substantially homogeneous isoelectric point.

By «factor VII» or «FVII», is meant the polypeptides comprising the sequence 1-406 of the human factor VII of the wild type (as for example described in U.S. Pat. No. 4,784,950 A of ZymoGenetics Inc.), or of the factor VII derived from another species (for example, bovine, porcine, rabbit, caprine, murine species). It further comprises natural allelic variations of the factor VII which may exist. The term «factor VII» also includes the variants of FVII which have the same activity or a higher biological activity as compared with the activity of the wild form, these variants notably including the polypeptides which differ from wild FVII by insertion, deletion or substitution of one or several amino acids.

The term of «factor VII» or «FVII» also comprises the non-cleaved factor VII (zymogen) and the activated factor VII («factor VIIa» or «FVIIa»). In a preferred embodiment of the invention, the factor VII used in the composition according to the invention is preferably activated.

By the expression «biological activity of the factor VIIa», is understood the capability of FVIIa of generating thrombin, for example at the surface of activated platelets. The activity of the factor VII in the composition according to the invention may be evaluated in different ways.

The biological activity of FVIIa may for example be quantified by measuring the capability of an FVII composition of promoting blood coagulation by using a FVII- and thromboplastin-deficient plasma, as described for example in U.S. Pat. No. 5,997,864. In this test, the biological activity is evaluated relatively to a control sample and is converted into «FVII units» by comparison with a pooled standard human serum containing 1 unit/ml of Factor VII activity. Alternatively, the biological activity of the factor VII may be quantified (i) by measuring the capability of the Factor Vila of producing the factor Xa in a system comprising TF encompassed in a lipid membrane and some Factor X (Persson et al. J. Biol. Chem. 272:19919-19924, 1997): (ii) by measuring the hydrolysis of the factor X in an aqueous system (see «General methods» below); (iii) by measuring the physical bond of FVIIa to TF via surface plasmon resonance (Persson, FEBS letts, 413:359-363, 1997), (iv) by measuring the hydrolysis of a synthetic substrate or (v) by measuring the generation of thrombin in an in vitro system independent of TF.

In a particular embodiment, the factor VII of the invention is a recombinant factor VII. By «recombinant factor VII», is meant any factor VII stemming from genetic engineering and resulting from the expression of the corresponding gene in any microorganism, plant, transgenic plant, animal or transgenic animal. By microorganism, is meant any bacterial, fungal, viral or cellular system. The recombinant factor VII may also be produced from eukaryotic cells in culture such as plant or mammal cells, for example animal or human cells.

Thus, the FVII of the invention is derived from transcription and translation of a DNA molecule encoding FVII in a host cell. The recombinant FVII of the invention may be obtained using standard techniques, well known to those skilled in the art, allowing expression of a protein in a biological system.

More specifically, the term "recombinant FVII" means any FVII obtained by genetic recombination and expressed in a cell line that is cultured. Examples are the following lines: BHK (Baby, Hamster Kidney) and notably BHK tk "ts13 (CRL 10314, Waechter and Baserga, Proc Natl Acad Sci USA 79:1106-1110, 1982 . . . ), CHO (ATCC CCL 61), COS-I (ATCC CRL 1650), HEK293 (ATCC CRL 1573. Graham et al, J. Gen. Virol 36:59-72, Gen 1977), Rat Hep I (Rat hepatoma; ATCC CRL 1600), Rat Hep II (Rat hepatoma, ATCC CRL 1548), TCMK (ATCC CCL 139), Human lung (ATCC HB 8065), NCTC 1469 (ATCC CCL 9.1) and DUKX cells (CHO cell line) (Urlaub and Chasin, Proc Natl Acad Sci USA 77:4216-4220 1980), 3T3 cells, Namalwa cells, or BHK cells adapted to culture without serum (U.S. Pat. No. 6,903,069).

In a particular embodiment, the cell line is modified so as to produce compositions according to the invention, for example by modulating the expression of a glycosyltransferase, in particular over-expressing a sialyltransferase.

In a particular embodiment, the factor VII of the invention is a transgenic factor VII. By «transgenic factor VII», is meant any recombinant factor VII obtained from a transgenic animal.

By «transgenic animal», is meant any non-human animal having a modification of its genome intended for allowing expression of the factor VII according to the invention. The modification of the genome advantageously results from an alteration, a modification or the insertion of a gene. This modification may be due to the action of conventional altering agents or mutagens or else carried out by directed mutagenesis. The modification of the genome may also result from insertion of gene(s) or replacement of gene(s) in its (their) wild or mutated form. In a preferred embodiment, the factor VII of the present invention is obtained from milk of a transgenic animal. A transgenic animal according to the invention be selected from rabbits, goats, cows, camels, hamsters, mice, rats, horses, sows, dromedaries, ewes, llamas, the list not being a limitation. Preferably, the factor VII of the present invention is obtained from the milk of transgenic rabbits. The secretion of the factor VII by the mammary glands, allowing its secretion in the milk of the transgenic mammal, involves the control of the expression of the factor VII in a tissue-dependent way. Such control methods are well known to one skilled in the art. The control of the expression is carried out by sequences allowing expression of the protein towards a particular tissue. These are notably WAP, beta-casein, beta-lactoglobulin promoter sequences and signal peptide sequences, the list not being a limitation. Particularly advantageously, expression in the mammary glands of the rabbits is performed under the control of the promoter of beta-casein, well known to those skilled in the art.

A method for producing a recombinant protein in the milk of a transgenic animal can include the following steps: a synthetic DNA molecule comprising a gene coding for human FVII, this gene being under the control of a promoter of a protein naturally secreted into the milk is integrated into an embryo of a non-human mammal. The embryo is then placed in a female mammal of the same species. Once the mammal derived from the embryo has sufficiently developed, the lactating mammal is induced, then the milk is collected. The milk then contains the FVII of interest secreted by the transgenic animal.

A protein preparation example in the milk of a mammal female other than the human being is given in the application EP 0 527 063 B 1 (Institut National de la Recherche Agronomique (National Institute for Agronomic Research)), the teaching of which may be used again for producing the factor VII of the invention.

In a preferred embodiment, the factor VII according to the invention is produced in the milk of transgenic rabbits. In particular, a plasmid containing the beta-casein promoter is prepared by introduction of a sequence comprising the promoter of the beta-casein gene, the plasmid being constructed so as to receive a foreign gene placed under the control of this promoter. The gene encoding for the human factor VII is integrated, and placed under the dependency of the beta casein promoter. The plasmid containing the promoter and the sequence encoding the protein of interest is digested with restriction enzymes to release the DNA fragment containing the beta-casein promoter and the sequence of human FVII. After purification, fragments are introduced by microinjection into the male pronucleus of wild-type (WT) rabbit embryos. Embryos are then cultivated before being transfer into the oviduct of wild-type females that are hormonally prepared. At dropping of the females, the descendants are evaluated by PCR to determine transgenic animals. The copy number of the transgenes and their integrity is revealed by Southern techniques from DNA extracted from the transgenic baby rabbits obtained. Concentrations in human milk of transgenic animals FVII are measured using specific radioimmunoassay tests.

In a particular embodiment, the composition of factor VII according to the invention is obtained by the method comprising the steps of:

(a) inserting a DNA sequence comprising a gene encoding the factor VII in an embryonic non-human mammal, said gene being under the transcriptional control of the beta-casein promoter, (b) transferring the embryos obtained in step a) into the oviduct of a female non-human mammal so that it develops into an adult mammal, (c) inducing lactation in the adult non-human mammal obtained in step b) of the female type or in a female descendant of the non-human mammal wherein the gene and promoter are present in its genome, (d) collecting the milk of said non-human mammal, and (e) purification of factor VII present in the milk collected.

In a particular embodiment, the adult non-human mammal or the female descendant of the non-human mammal is selected notably for its capacity to produce factor VII compositions according to the invention. The transgenic animal can also be selected according to others criteria, as for example the presence of only one integration site and/or the integrity of the product.

In a particular embodiment, the insertion of a DNA sequence comprising a gene coding for factor VII in an embryonic non-human mammal, said gene being under the transcriptional control of the beta-casein promoter is by microinjection more particularly in the male pronucleus of a rabbit embryo.

By "embryo", is meant the male or female pronucleus of an embryo of non-human mammal, more particularly of rabbit, fertilized.

By «isoelectric point» or «pI», is meant the pH for which the net elementary charge of the factor VII or factor VIIa molecule is zero, i.e. the pH at which the molecule is electrically neutral (zwitterionic form). The isoelectric point of the factor VII according to the invention may be measured by applying a technique well known to one skilled in the art, such as isoelectric focusing («IEF»). This electrophoretic technique allows separation of the proteins on the basis of their isoelectric point. It consists in a migration induced by a uniform electric current, of proteins in a pH gradient until they reach a pH equivalent to their specific isoelectric point, a moment at which they cease migration since their net charge is zero. IEF gels are used for determining the isoelectric point of a given protein and for detecting minor changes of the latter due to post-translational modifications such as γ-carboxylations, phosphorylations or glycosylations.

By «substantially homogeneous», is meant that at least 90%, preferably at least 95% of the factor VII molecules of the composition have an isoelectric point comprised in a pH unit interval of less than or equal to 1.2. In another embodiment of the invention at least 50%, preferably at least 55%, preferably 60%6 of the factor VII molecules of the composition have an isoelectric point comprised in a pH unit interval of less than 1; preferably less than 0.5. In another preferred embodiment, at least 50%, preferably at least 55%, preferably 60% of the factor VII molecules of the composition have an isoelectric point comprised in a pH unit interval of 0.4.

By «N-glycan forms», is meant the whole of the N-glycan forms present on both N-glycosylation sites of the factor VII of the invention.

N-glycan forms are said to be monocharged, if their total charge is equal to 1. In the sense of the present invention, by «charge», is meant a phosphate group, a sulfate group, or a sialic acid molecule. Thus, the N-glycan forms are said to be monocharged, if they only contain a phosphate group or a sulfate group or a sialic acid molecule. As opposed to the term of «monocharged», the term of «bicharged» means that the total charge borne by the N-glycan forms is equal to 2, i.e. they have two charges selected from a phosphate group, a sulfate group and/or a sialic acid molecule. In other words, the N-glycan bicharged forms have either a sialic acid molecule and a phosphate group, or a sialic acid molecule and a sulfate group, or two sialic acid molecules, or two phosphate groups, or two sulfate groups, or a phosphate group and a sulfate group. The term of «neutral» as for it, means that the N-glycan forms do not contain any charge.

The charge of the N-glycan forms of the factor VII according to the invention may be measured by applying a technique well known to one skilled in the art, notably by ultra-high performance liquid chromatography with an anion exchanger resin coupled with detection by fluorescence (AEX-UPLC/FD). With this method it is possible to separate the different N-glycan forms according to their apparent charge (see in particular Hermentin et al., Glycobiology, Vol. 6, No. 2, 1996). Within the scope of anion exchange chromatography, a positively charged resin is used as a stationary phase. These positively charged resins generally consist of a cross-linked polymer or gel, on which are grafted positively charged groups. In an advantageous embodiment of the invention, a low anion exchange column of the amino propyl type is used.

The applicant has more particularly demonstrated that the substantially homogeneous isoelectric point of the composition of factor VII according to the invention results from the combination of the glycosylation and γ-carboxylation properties of the FVII molecules which make it up.

The factor VII molecules which form the composition according to the invention include, similarly to the human plasma factor VII, two N-glycosylation sites in the positions 145 and 332, and 2 sites of O-glycosylation, in the positions 52 and 60. Each of these sites may receive «glycans» or «sugar chains» or «oligossacharide chains». The N-glycosylated and/or O-glycosylated oligosaccharide chains borne by each Factor VII molecule of the composition may differ from one molecule to another. However, it is possible to measure the distribution of each unit in the factor VII composition according to the invention by using techniques known to one skilled in the art.

In the case of the factor VII composition according to the invention, it appears that among all the N-glycan forms of the factor VII of the composition, at least 60% of the N-glycan forms, preferably at least 65%, preferably at least 70%, preferably at least 75%, preferably at least 80%, preferably at least 85%, preferably at least 90%, preferably at least 95%, are monocharged. In a preferred embodiment, the factor VII molecules having monocharged N-glycan forms represent between 60% and 95% of the factor VII molecules of the composition, preferably between 65% and 90% of the factor VII molecules of the composition, preferably between 70% and 85% of the factor VII molecules of the composition, preferably between 70% and 80% of the factor VII molecules of the composition, preferably between 74% and 77% of the factor VII molecules of the composition.

In the case of the composition of Factor VII according to the invention, it appears that among all the N-glycan forms of Factor VII of the composition, between 3% and 10%, preferably between 3% and 7% of the N-glycan forms are neutral.

In the case of the composition of Factor VII according to the invention, it appears that among all the N-glycan forms of Factor VII of the composition, between 15% and 25%, preferably between 18% and 22% of the N-glycan forms are bicharged.

In the case of the composition of factor VII according to the invention, it appears that among all the N-glycan forms of factor VII of the composition, less than 5%, preferably less than 2%, preferably less than 1% of the N-glycan forms are tricharged.

In the case of the composition of factor VII according to the invention, it appears that among all the N-glycan forms of factor VII of the composition, less than 5%, preferably less than 2%, preferably less than 1% of the N-glycan forms are tetracharged.

For the purposes of the invention, it is understood that the percentages cited above do not therefore take into account glycan forms involved in O-glycosylation.

Moreover, the factor VII molecules forming the composition of the invention only comprise sialic acids bound through bounds of the α2-6 type. The applicant also noticed that the fucose content of the factor VII had not effect on the isoelectric point of the composition of factor VII.

In the case of the factor VII composition according to the invention, it appears that at least 60%, preferably at least 65%, preferably at least 70% of the N-glycan forms of the factor VII of the composition are monosialylated complexes.

The complex N-glycan forms are forms well known to one skilled in the art (see in particular. Kornfeld R et al, *Annual Review of Biochemistry*. 1985; 54:631-64. Assembly of asparagine-linked oligosaccharides).

In a particular embodiment, at least 10%, preferably at least 15%, preferably at least 20%, preferably at least 25% of the N-glycan forms of the factor VII of the composition are high Mannose/hybrid.

By «γ-carboxylation», is meant the product of a biochemical reaction aiming at transforming a plurality of glutamic acid residues present in the peptide sequence of the factor VII into carboxy-glutamic acid or "GLA" residues.

Advantageously, the factor VII molecules which form the composition according to the invention have, for at least 80% of them, γ-carboxylation on nine residues of glutamic acid. In another embodiment, at least 85% of said molecules have γ-carboxylation on nine residues of glutamic acid. In another embodiment, between 85% and 100%, preferably between 90% and 100%, preferably between 95% and 100% of said molecules have γ-carboxylation on nine residues of glutamic acid. Advantageously, the γ-carboxylation level on the residue of glutamic acid 35 ($Glu_{35}$) of the factor VII molecules of the composition is less than 20%. In another embodiment, the γ-carboxylation level of the residue $Glu_{35}$ is less than 15%, preferably less than 10%, preferably less than 5%.

The applicant surprisingly discovered that it is the specific combination of the level of the monocharged N-glycan forms and of the γ-carboxylation level, which is responsible for the substantial homogeneity of the isoelectric points of the factor VII molecules forming the composition according to the invention.

The FVII composition according to the invention may advantageously be formulated without causing precipitation of the FVII molecules which make it up. Indeed, it is known that at the isoelectric point of the molecule, the latter aggregates and precipitates. The factor VII molecules which form the composition according to the invention have an isoelectric point comprised between 6.6 and 7.0. The result of this is better stability of the factor VII composition according to the invention, notably when the latter is formulated at a pH below the isoelectric point, and in particular at a pH of 6. The improvement of the stability of the factor VII composition according to the invention gives the possibility of avoiding the electrostatic interactions responsible for precipitation and aggregation phenomena of the soluble and insoluble type, as well of avoiding the loss of active raw materials and therefore a lowering of the yield resulting in a quantitative loss of active ingredients and therefore potentially in a loss of activity.

Another object of the invention concerns a purification method for the activated factor VII according to the invention.

The milk of transgenic rabbits is obtained from the line of transgenic rabbits R69. The frozen milk of transgenic rabbits is defrosted and concentrated in the form of a milk pool from transgenic rabbits.

The thereby obtained milk pool from transgenic rabbits is then subject to a clarification step using a filter in depth having a porosity of 0.2 μm, in order to remove the lipids and insoluble compounds. The thereby clarified milk is then subject to a viral inactivation step by treatment with a solvent of the detergent type, for example Polysorbate 80 or Tri-n-Butyl Phosphate at 25° C.±2° C. for at least two hours. Such a treatment notably gives the possibility of efficiently inactivating viruses, and in particular the viruses of the non-enveloped viruses type. The clarified and virally inactivated milk is then subject to an affinity chromatography step using a specific affinity ligand of the factor VII/factor VIIa. The eluate of factor VII obtained at the end of this chromatography step is then subject to an ultra-filtration and formulation step, thereby giving the possibility of obtaining an intermediate factor VII concentrate having a purity of 95%.

The intermediate factor VII concentrate is then subject to a filtration step using a filter having a porosity from 0.2 μm to 0.2 μm followed by a nanofiltration step on filters having a porosity of 20 nm and then of 15 nm. The thereby obtained product and containing the factor VII is then subject to a chromatography step of the Q Sepharose XL gel type and then to a chromatography step of the CHT-I type followed by chromatography of the SEC Superdex 200 type. The thereby obtained concentrate of factor VII is then subject to a stabilization step and then to a filtration step on a filter having a porosity of 0.2 μm.

The thus described method gives the possibility of obtaining a factor VII concentrate having a purity of about 99.9995%.

In a preferred embodiment, the method of purification and extraction of the factor VII is the one described in application EP12305882.

Another object of the present invention relates to a method for formulating an activated factor VII composition according to the invention.

Advantageously, the formulation method used is the one described in application WO2010/149907.

This method notably comprises the mixing of the activated factor VII composition according to the invention with a buffer solution, adjustment of the pH if required, filtration and drying if necessary for obtaining the solid form.

In a preferred embodiment, the step for mixing the activated factor VII composition with a buffer solution is applied in chromatography of the gel permeation type. The term of «buffer solution» includes at least one hydrophilic amino acid or bearing a positively charged side chain, and an alkaline metal salt, an earth alkaline metal salt, or a transition metal salt. Mention may notably be made of trisodium citrate, calcium chloride, or zinc chloride. Preferably the salt used is preferentially sodium citrate or calcium chloride. Advantageously, the buffer solution also contains at least one hydrophobic amino acid.

Advantageously, the buffer solution comprises one or several of the constituents selected from:
one salt, preferably a citrate salt, preferably trisodium citrate;
an amino acid, or a hydrophilic amino acid salt, preferably a hydrophilic amino acid salt, preferably arginine hydrochloride and/or lysine hydrochloride;
an amino acid or a hydrophobic amino acid salt, preferably a hydrophobic amino acid, preferably isoleucine and/or glycine.

Finally, the composition of the invention may comprise one or several detergents of the non-ionic type such as polysorbates, polyoxamers, polyoxyethylene alkyl ethers, an ethyl/polypropylene block copolymer and polyethylene glycol. Advantageously, the preferred detergents are polysorbate 80 and polysorbate 20.

Advantageously, the factor VII composition obtained at the end of the mixing step with the buffer solution comprises:
the factor VII according to the invention, preferably in activated form;
from 10 to 40 g/l of arginine, optionally as a hydrochloride;
from 4.2 to 6.6 g/l of isoleucine;
from 0.6 to 1.8 of lysine;
from 0.6 to 1.8 g/l of glycine;
from 1 to 2 g/l of trisodium citrate dehydrate or from 0 to 0.2 g/l of calcium chloride dihydrate; and if necessary from 0 to 0.5 g/l of polysorbate 80.

According to a particular example, the factor composition obtained at the end of the mixing step with the buffer solution comprises some factor VII (preferably as factor VIIa) at a concentration from 0.2 to 2 g/l, arginine hydrochloride at 24 g/l, isoleucine at 6 g/l, trisodium citrate dehydrate at 1.5 g/l, glycine at 1.2 g/l, lysine hydrochloride at 1.2 g/l and/or polysorbate 80 at 0.07 g/l.

In a particular example, the composition of factor obtained after the step of mixing with the buffer solution comprises factor VII (preferably in the form of factor VIIa) at 0.2 to 2 g/l, arginine hydrochloride at 24 g/l, isoleucine at 6 g/l, dehydrated trisodium citrate at 1.5 g/l, glycine at 1.2 g/l, lysine hydrochloride at 1.2 g/l, and/or polysorbate 80 at 0.09 g/l.

According to another particular example, the factor VII composition obtained at the end of the mixing step with the buffer solution comprises the factor VII (preferably as factor VIIa) at a concentration from 0.2 to 2 g/l, arginine hydrochloride at 34 g/l, calcium chloride dihydrate at 0.15 g/l, isoleucine at 6 g/l.

Preferably, the factor VII composition according to the invention is without any sugar, polyol or methionine. The sugars to be avoided notably include, in addition to saccharose, di- and tri-saccharides and polysaccharides, such as dextrose, lactose, maltose, trehalose, cyclodextrins, maltodextrins and dextrans. The polyols to be avoided notably include sorbitol and xylitol in addition to mannitol.

Still preferably, the composition is without glycylglycine. Still preferably, the composition is without glycylglycine.

According to a preferred embodiment, the composition of the invention is further without any antioxidant. The antioxidants for example include one or several of the following compounds: homocysteine, cysteine, cystathionine, methionine, glutathion.

The pH of the solution before drying is preferably comprised between 4.0 and 9.0, more particularly in the ranges 4.0 and 8.0; 4.0 and 7.5; 4.5 and 7.5; 5.0 and 7.5; 5.5 and 7.0; 6.0 and 7.5; 6.5 and 7.5.

Drying is a method for removing water extensively. This is dehydration aiming at removing as much water as possible. This phenomenon may be natural or forced. This drying may be achieved by freeze-drying, atomization and cryoatomization techniques. The preferred method for obtaining the solid form of the composition for pharmaceutical use according to the invention is freeze drying. Freeze-drying methods are well known to one skilled in the art, see for example [Wang et al., Lyophilization and development of solid protein pharmaceuticals, International Journal of Pharmaceutics, Vol. 203, p 1-60, 2000].

Other suitable methods for reducing the humidity level of the water content of the composition may be contemplated. Preferably, the humidity level is less than or equal to 3% by weight, preferably less than or equal to 2.5% by weight, preferably less than or equal to 2%, preferably less than or equal to 1.5%.

Preferably, the formulation method further comprises a step for eliminating or inactivating infectious agents, for example by dry heating the lyophilizate.

Preferably, the formulation method further comprises a step for filtering the factor VII composition and/or a step for freeze-drying the formulated factor VII composition.

The factor VII composition according to the invention is particularly advantageous when it is formulated according to the method described above. Indeed, the formulation method according to the invention applied to the factor VII composition according to the invention allows improvement of its stability.

Another object of the invention relates to the use of the factor VII composition of the invention as a drug, for the treatment of bleeding episodes.

Another object of the invention relates to the use of the factor VII composition according to the invention for preventing hemorrhages occurring during surgical operations and invasive procedures.

Another object of the invention is a pharmaceutical composition comprising the factor VII composition according to the invention and an excipient and/or a pharmaceutically acceptable carrier.

The excipient may be any solution, such as a saline, physiological, isotonic or buffered solution as well as any suspension, gel or powder compatible with pharmaceutical use and known to one skilled in the art. The compositions according to the invention may further contain one or several agents or carriers selected from dispersants, solubilizers, stabilizers, surfactants and preservatives. On the other hand the composition according to the invention may comprise other active agents or ingredients.

Moreover, the compositions may be administered in different ways and in different forms. The administration may be carried out via any conventional route for this type of therapeutic approach, such as notably via a systemic route, in particular by intravenous, intradermal, intra-tumoral, subcutaneous, intra-peritoneal, intramuscular or intra-arterial injection. Mention may be made for example of intra-tumoral injection or injection in an area close to the tumor or irrigating the tumor.

The dosages may vary according to the number of administrations, to the combination with other active ingredients, to the development stage of the pathology, etc.

Of course, the present invention is not limited to the described and illustrated examples and embodiments, but it is subject to many alternatives accessible to one skilled in the art.

EXAMPLES

Example 1: Production of Transgenic Rabbits Producing Human FVII Protein in their Milk An expression vector comprising a beta-globin insulating sequence from chicken, the control region of goat beta-casein at 5', an optimised cDNA sequence for the expression in mammal cells coding for human FVII and the non-translated region of beta-casein at 3' was prepared in a SuperCos backbone. The assembly in FIG. 6 represents the construction vector.

The transgene was prepared from the digestion of the construction vector with the NotI restriction endonuclease to release the SuperCos backbone and linearized the expression vector. The resulting fragments were separated by gel electrophoresis, purified from the gel and used for microinjection.

To produce transgenic rabbits, the microinjection of the transgene into male pronuclei of embryos fertilized collected from WT rabbits was performed. After a period of in vitro culture of a few hours, the microinjected male pronuclei of embryos were transferred into the oviduct of female non-transgenic rabbits hormonally prepared. After gestation, the progeny are obtained. A genetic analysis allows the evaluation of the presence of the human factor VII transgene by PCT analysis using primers specific from human factor VII sequence. The presence of the transgene and its integrity has been revealed by the Southern blotting technique from DNA extracted from the transgenic baby rabbits obtained. A phenotypic analysis allows the evaluation of the human factor VII concentration expressed in the milk of transgenic female rabbits. This measure is realized by enzyme immunoassay (ELISA) using commercial reagents (Diagnostica Stago). Briefly, the factor VII to be assayed is captured by a human anti-factor VII antibody immobilized on a solid phase. The factor VII fixed was then recognized by a known immuno-peroxidase conjugate. The rate of bound peroxidase is measured by its activity on the ortho-phenylenediamine substrate in the presence of hydrogen peroxide. The intensity of the coloration, after stopping the reaction with a strong acid, is a function of the amount of factor VII initially present in the sample.

Example 2: Purification and Extraction of the Obtained Factor VII

The method for purifying and extracting the factor VII applied in this example is described below.

The milk of transgenic rabbits is obtained from the line of transgenic rabbits R69. The frozen milk of transgenic rabbits is defrosted and concentrated in the form of a milk pool from transgenic rabbits.

The thereby obtained milk pool from transgenic rabbits is then subject to a clarification step using a filter in depth having a porosity of 0.2 µm, in order to remove the lipids and insoluble compounds. The thereby clarified milk is then subject to a viral inactivation step by treatment with a solvent of the detergent type, for example Polysorbate 80 or Tri-n-Butyl Phosphate at 25° C.±2° C. for at least two hours. Such a treatment notably gives the possibility of efficiently inactivating viruses, and in particular the viruses of the non-enveloped viruses type. The clarified and virally inactivated milk is then subject to an affinity chromatography step using a specific affinity ligand of the factor VII/factor VIIa. The eluate of factor VII obtained at the end of this chromatography step is then subject to an ultra-filtration and formulation step, thereby giving the possibility of obtaining an intermediate factor VII concentrate having a purity of 95%.

The intermediate factor VII concentrate is then subject to a filtration step using a filter having a porosity from 0.2 µm to 0.2 µm followed by a nanofiltration step on filters having a porosity of 20 nm and then of 15 nm. The thereby obtained product and containing the factor VII is then subject to a chromatography step of the Q Sepharose XL gel type and then to a chromatography step of the CHT-I type followed by chromatography of the SEC Superdex 200 type. The thereby obtained concentrate of factor VII is then subject to a stabilization step and then to a filtration step on a filter having a porosity of 0.2 µm.

The thereby described method gives the possibility of obtaining a factor VII concentrate having a purity of about 99.9995%.

The method for extracting and purifying factor VII is described in greater detail in European application EP12305882.

In the examples appearing in the present application, the recombinant activated factor VII available on the market (Novoseven®), produced by genetic engineering from BKH kidney cells of newborn hamsters is called «FVII-rec».

Example 3: Study of the Chare Profiling of N-glycans

A Identification and Quantification of N-Bound Oligosaccharides by High Performance Liquid Chromatography with Normal Phase Polarity in the HILIC Mode Coupled with Fluorimetric Detection (HILIC-HPLC/FD), a so-Called «HILIC» Method.

The hydrophilic interaction chromatography method (HILIC or Hydrophilic Interaction Chromatography) is an alternative of normal phase (NP) chromatography and allows sufficient separation of the polar species by avoiding the drawbacks related to the use of solvents which are not miscible in water. The stationary phase is a polar material generally based on silica or polymeric supports grafted through a functional group such as a cyano, amino, diol, amide group etc. and the mobile phase is organic and contains water as a strong eluent.

The factor VII is first of all subject to enzymatic digestion with PNGase F in order to specifically release the N-glycan derivatives.

The latter are isolated by extraction on a solid phase (SPE) and then labeled with a fluorophore: 2-aminobenzamide (2-AB) according to Bigge et al. (Bigge, J. C., et al., Non-selective and efficient fluorescent labeling of glycans using 2-aminobenzamide and anthranilic acid, Anal. Biochem., 230, 229-238 (1995)). Analysis of the N-glycan derivatives is finally carried out with HILIC-HPLC/FD according to Guile et al. (Guile, G. R., et al., A rapid and high-resolution high-performance liquid chromatographic method for separating glycans mixtures and analyzing oligosaccharide profiles, Anal. Biochem., 240, 210-226 (1996)). Detection is ensured by fluorescence at the wavelengths of a excitation=330 nm and λ emission=420 nm.

The results obtained for the factor VII of the invention as well as for the FVII-rec are shown in the tables below.

TABLE 1

Quantification of neutral, nanocharged and bicharged N-glycan forms of the factor VII of the invention obtained by the HILIC method

| N-glycan forms (expressed in %) | FVII (Batch 1) | FVII (Batch 2) | FVII (Batch 3) |
|---|---|---|---|
| Neutral | 3.6 | 4.3 | 3.9 |
| Monocharged | 75.5 | 74.6 | 75.3 |
| Bicharged | 21.0 | 21.2 | 20.6 |

The results obtained by the HILIC method show that the factor VII of the invention has a level of neutral N-glycan forms comprised between 3.6% and 4.3%, of monocharged N-glycan forms comprised between 74.6% and 75.5% and of bicharged N-glycan forms comprised between 20.6% and 21.2%.

TABLE 2

Quantification of the neutral, monocharged and discharged, tricharged, tetracharged N-glycan forms of the factor VII-rec obtained by the HILIC method.

| N-glycan forms (expressed in %) | FVII-rec | FVII-rec (results from the publication of Klausen et al.*) |
|---|---|---|
| Neutral | 11.3 | 9.4 |
| Monocharged | 25.1 | 27.9 |
| Bicharged | 55.1 | 51.2 |
| Tricharged | 7.3 | 11.6 |
| Tetracharged | 0.7 | 0 |

(*Klausen et al., Analysis of the site-specific asparagine-linked glycosylation of recombinant human coagulation factor VIIa by glycosidase digestions, liquid chromatography, and mass spectrometry, Mol Biotechnol. 1998 June; 9(3): 195-204.).

The results obtained by the HILIC method show that the neutral N-glycan forms of FVII-rec represent 11.3% of the N-glycan forms of the FVII-rec, that the monocharged N-glycan forms represent 25.1% of the N-glycan forms of the FVII-rec, and that the bicharged N-glycan forms represent 55.1% of the N-glycan forms of the FVII-rec. Further, the factor FVII-rec has a non-negligible amount of tricharged and tetracharged forms.

The results thereby obtained by the HILIC method are therefore compliant with those shown in the publication of Klausen et al.

B Identification and Quantification of N-Bound Oligosaccharides by the AEX/UPLC/FD Method The separation of the N-glycans according to their charge is carried out by AEX-UPLC/FD profiling of the derived N-glycans labeled with 2-AB. The operating procedure for preparing the derived N-glycans labeled with 2-AB is identical with the one described earlier for analyzing N-glycans by HILIC-HPLC/FD.

The profiling of the charge of the N-glycans of FVII by AEX-UPLC/FD was achieved by means of a low anion exchange column of the aminopropyl type. The glycans are separated according to their charge by applying an increasing gradient of ammonium formate. The detection of the derivative is carried out at the following wavelengths: excitation wavelength: 330 nm and emission wavelength: 420 nm. The profile obtained by AEX-UPLC/FD for the FVII (batch 1) is shown in FIG. 3.

The obtained results are shown in Table 3 below.

TABLE 3

Quantification of the neutral, monocharged and bicharged N-glycan forms obtained for the factor VII of the invention by the AEX-UPLC/FD method

| N-glycan forms | Retention time | FVII (batch 1) expressed in % | FVII (batch 2) expressed in % | FVII (batch 3) expressed in % |
|---|---|---|---|---|
| Neutral | 2-6 mm | 4.0 | 4.2 | 3.4 |
| Monocharged | 11-14 min | 76.5 | 76.9 | 77.2 |
| Bicharged | 17-20 min | 19.6 | 18.9 | 19.4 |

It is observed that the percentage of monocharged N-glycan forms of the three batches of FVII according to the invention is comprised between 76 and 78%.

Both of these orthogonal methods (HILIC and AEX) show that at least 74.6% of the N-glycan forms of factor VII of the invention are monocharged, independently of the measuring method used.

C Identification, Quantification and Comparison of N-Linked Oligosaccharides by the AEX/UPLC/FD Method for Factor VII of the Invention, Factor VII from Application WO2007/138199 and Factor VII-Rec.

The procedure used is the same as that described in Example 3. Profiling of N-glycan charge of FVII by AEX-UPLC/FD was performed on the factor VII from the invention, factor VII derived from application WO2007/138199 and factor VII-rec.

Glycan profiles are presented in FIG. 5. FIG. 5A shows the glycan profile of FVII resulting from application WO2007/138199. FIG. 5B shows the glycan profile of FVII of the invention and FIG. 5C shows the glycan profile of FVII-rec.

TABLE 4

Quantification of neutral, monocharged and bicharged N-glycanic forms obtained by the AEX-UPLC/FD method

| N-glycanic forms | Retention time | FVII from the invention (batch 4) expressed in % | FVII (originating from application WO2007/138199) expressed in % | Factor VII-rec expressed in % |
|---|---|---|---|---|
| Neutral ($Z_0$) | 3-5 min | 7.0 | 3.0 | 7.0 |
| Monocharged ($Z_1$) | 5-7 min | 73.0 | 51.0 | 29.0 |
| Bicharged ($Z_2$) | 7-10 min | 20 | 39.0 | 54.0 |
| Tricharged ($Z_3$) | 10-12 min | 0.0 | 7.0 | 9.0 |
| Tetracharged ($Z_4$) | 12-14 min | 0.0 | 0.0 | 1.0 |

As regards the FVII resulting from application WO2007/138199, the results obtained using the AEX/UPLC/FD method show:
that neutral N-glycan forms of FVII resulting from application WO2007/138199 represent 3% of N-glycan forms of this FVII,
that monocharged N-glycan forms represent 51% of the N-glycan forms of this FVII and,
that bicharged N-glycan forms represent 39% of the N-glycan forms of this FVII,
a non-negligible amount of tricharged forms.
The results obtained using the AEX/UPLC/FD method show that neutral N-glycan forms of FVII-rec represent 7.0% of N-glycan forms of FVII-rec, that monocharged N-glycan forms represent 29.0% of the N-glycan forms of FVII-rec, and that bicharged N-glycan forms represent 54.0% of the N-glycan forms of FVII-rec. In addition, the factor VII-rec has a non-negligible amount of tricharged and tetracharged forms.

Example 4: Identification, Quantification and Comparison of the N-Glycan

Forms of factor VII according to the invention and factor VII resulting from PCT Application WO2007/138199 by the HILIC method A Quantification of Factor VII N-Glycan Forms According to the Invention Carried Out Using the HILIC Method.

The quantification of the N-glycan forms of the factor VII according to the invention is achieved by means of the HILIC method as described in Example 3.

The thereby obtained results are shown in Table 5.

TABLE 5

Quantification of the N-glycans obtained for the factor VII composition of the invention.

| N-glycan forms (expressed in %) | FVII (batch 1) | FVII (batch 2) | FVII (batch 3) | Charge |
|---|---|---|---|---|
| A1G0 | 0.5 | 0.8 | 0.5 | 0 |
| Man5 | 1.3 | 1.5 | 1.4 | 0 |
| Man4-A1G1 | 0.2 | 0.4 | 0.4 | 0 |
| A2G2 | 1.4 | 1.1 | 1.2 | 0 |
| A1G1S1 | 1.1 | 1.2 | 1.2 | 1 |
| A2G2F | 0.5 | 0.4 | 0.4 | 0 |
| A2G1S1 | 0.5 | 0.7 | 0.3 | 1 |
| Man4-A1G1S1 | 2.8 | 2.9 | 4.2 | 1 |
| Man6PGlcNAc | 9.8 | 9.1 | 9.9 | 1 |
| A2G2S1 | 43.3 | 41.8 | 41.1 | 1 |
| A2G2S1-SO3H | 0.9 | 0.9 | 0.9 | 2 |
| Man5-A1G1S1 | 0.2 | 0.4 | 0.2 | 1 |
| A2G2FS1 | 8.8 | 9.3 | 9.9 | 1 |
| Man7PGlcNAc | 2.8 | 3.2 | 3 | 1 |
| A2G2FS1* | 2 | 2.3 | 1.9 | 1 |
| Man7PGlcNAc* | 1.7 | 1.6 | 1.6 | 1 |
| A2G2F2S1 | 2.2 | 2.2 | 2 | 1 |
| A2G2S2 | 9.1 | 9.7 | 8.8 | 2 |
| Man7(PGlcNAc)2 | 3.4 | 2.8 | 3.2 | 2 |
| A2G2FS2 | 2.6 | 3.1 | 2.8 | 2 |
| Man6PGlcNAc-A1G1S1 | 5 | 4.7 | 4.9 | 2 |
| High-Mannose/Neutral Hybrid | 1.5 | 1.9 | 1.8 | 0 |
| High-Mannose/Monocharged Hybrid | 17.3 | 17.2 | 18.9 | 1 |
| High-Mannose/Bicharged Hybrid | 8.4 | 7.5 | 8.1 | 2 |
| Total High-Mannose/Hybrid | 27.2 | 26.6 | 28.8 | — |
| Monocharged N-glycan forms | 75.2 | 74.7 | 75.4 | 1 |
| Monosialylated Complex | 58.8 | 58.4 | 57.3 | 1 |
| Bisialylated Complex | 11.7 | 12.8 | 11.6 | 2 |

*Isomeric forms

Quantitative analysis of the different glycan structures (Table 5) show that the N-glycan forms of the factor VII of the composition are in majority monosialylated complexes (around some 60%). The N-glycan forms of the high mannose/hybrid type are present at a minimum of 25%.

B Quantification of the Factor VII N-Glvcan Forms Resulting from Application WO2007/138199 Factor VII Carried Out Using the HILIC Method.

Quantification of factor VII N-glycan forms resulting from application WO2007/138199 is carried out using the HILIC method, as described in Example 3. The results thus obtained are shown in Table 6.

TABLE 6

Quantification of N-glycans obtained for the factor VII composition resulting from application WO2007/138199

| N-glycan forms (expressed in %) | FVII originating from International application WO2007/138199 | Charge |
|---|---|---|
| Man5 | 0.7 | 0 |
| A2G2 | 0.3 | 0 |
| A1G1S1 | 0.6 | 1 |
| Man5-A1G1 | 0.3 | 0 |
| A2G2F | 0.3 | 0 |
| A2G1S1 + A1G1FS1 | 0.4 | 1 |
| Man4-A1G1S1 | 0.8 | 1 |
| Man6PGlcNAc | 6.2 | 1 |
| Man6PGlcNAc* | 1.4 | 1 |
| A2G2S1 | 18.2 | 1 |
| A2G2FS1 | 9 | 1 |
| Man7PGlcNAc | 1.6 | 1 |
| A2G2FS1* | 4 | 1 |
| Man7PGlcNAc* | 0.6 | 1 |
| Monocharged HM/Hyb | 0.3 | 1 |
| A2G2F2S1 | 9.7 | 1 |
| A2G2S2 | 10.9 | 2 |
| A3G3S1 | 0.7 | 1 |
| Man7(PGlcNAc)2 | 2 | 2 |
| A2G2FS2 | 15.9 | 2 |
| A3G3F0-1S1 | 0.3 | 1 |
| A3G3F0-1S1* | 0.9 | 1 |
| A3G3F1-2S1 | 0.6 | 1 |
| Man6PGlcNAc-A1S1 | 4.3 | 2 |
| A3G3S2 | 1.8 | 2 |
| A3G3S2* | 0.5 | 2 |
| A3G3FS2 | 1 | 2 |
| A3G3FS2* | 1.1 | 2 |
| A3G3F0-2S2 | 0.7 | 2 |
| A3G3F0-2S2-3 | 0.7 | 3 |
| A3G3S3 | 2.8 | 3 |
| A3G3F0-2S3 | 1 | 3 |
| A3G3F0-2S3* | 0.3 | 3 |
| High-Mannose/Neutral Hybrid | 1 | 0 |
| High-Mannose/Monocharged Hybrid | 10.9 | 1 |
| High-Mannose/Bicharged Hybrid | 6.3 | 2 |
| Total High-Mannose/Hybrid | 18.2 | — |
| Monocharged N-glycannic forms | 55.3 | 1 |
| Monosialated complex | 44.4 | 1 |
| Bisialated complex | 31.9 | 0 |
| Neutral (Z0) | 2 | 0 |
| Monocharged (Z1) | 55 | 1 |
| Bicharged (Z2) | 38 | 2 |
| Tricharged (Z3) | 5 | 3 |

*Isomeric forms

The quantitative analysis of different glycan structures (Table 6) shows that the N-glycan forms of factors VII resulting from application WO2007/138199 are predominantly of the monosialylated complex type (at around about 45%). N-glycan forms of the High Mannose/hybrid type are present at around 18%.

Example 5: Quantification of the γ-carboxylations

The human factor VIIa has other post-translational modifications, such as the γ-carboxylation of the N-terminal GLA domain. For the plasma factor VII, the first ten glutamic acids are all γ-carboxylated (Jurlander B. et al., Recombinant activated factor VII (rFVIIa): characterization, manufacturing, and clinical development. Semin. Thromb. Hemost. 27.4 (2001): 373-84., while the tenth glutamic acid of NovoSeven® is only partly γ-carboxylated (Thim L. et al., Amino acid sequence and posttranslational modifications of human factor Vlla from plasma and transfected baby hamster kidney cells. Biochemistry. 27.20 (1988): 7785-93).

The study of the γ-carboxylations of factor VII of the invention was conducted by using the liquid phase chromatography method coupled with mass spectrometry as described below (LC-MS).

The factor VII is reduced and alkylated beforehand and then subject to enzymatic digestion by means of a specific enzyme of the trypsin type. The thereby generated peptides are analyzed by electrospray mass spectrometry after separation by reverse phase liquid chromatography of the C18 type (Yates, J. R., Ruse, C. I., Nakorchevsky, A., (2009) Proteomics by mass spectrometry: approaches, advances, and applications. Annu Rev Biomed Eng. 11, 49-79.). This approach gives the possibility of measuring the specific mass of the γ-carboxylated N-terminal peptide of the factor VII and of inferring therefrom its γ-carboxylation level.

FIG. 2 shows the mass spectrum of the N-terminal peptide [$Ala_1$-$Arg_{36}$]. The measured average mass is 4.768.0 Da, which is consistent with the theoretical mass of 4,768.0 Da (reduced and alkylated cysteines) which corresponds to 9 γ-carboxylations. The factor VII of the present invention therefore has 9 γ-carboxylations. FIG. 2 also contains the mass spectrum of the N-terminal peptide [$Ala_1$-$Lys_{32}$], which is eluted in a similar retention time. The molecular mass of the peptide is also consistent with the presence of 9 γ-carboxylations on the peptide. The conclusion may therefore be drawn that the factor VII of the invention has 9 γ-carboxylated glutamic residues on the ten potential sites, and that the glutamic residue located in position 35 relatively to the sequence of the human factor VII ($Glu_{35}$) is not γ-carboxylated.

Moreover, the peptide [$Asp_{33}$-$Gly_{47}$] was isolated by peptide mapping. This peptide contains the amino acid $Glu_{35}$ which was found in majority in the non-carboxylated form with a mass of 1,786.9 Da. A minority form of this peptide was discovered as a mass of 1,830.9 Da, corresponding to a modified $Glu_{35}$. This form is estimated at less than 5%, based on the MS signals. This result confirms the presence of γ-carboxylations on the first nine glutamic acids of the factor VII of the invention while the tenth is in majority not γ-carboxylated.

The distribution of the various isoforms of the factor VII of the invention was also studied by ion exchange chromatography, the procedure of which is described below. The same study was conducted on FVII-rec.

Briefly, the isoforms of the factor VII are separated on a strong anion exchange column (SAX). A sample of factor VII is first loaded on a column (Mono Q 5/50 GL, GE Healthcare) equilibrated beforehand to pH 9 with a 20 mM Tris buffer. The sample is then eluted by applying an increasing gradient of an elution buffer of the 20 mM Tris/1M NaCl type at pH 9.

TABLE 7

Quantification of the isoforms of the factor VII of the invention and of FVII-rec - Integration of the peaks observed on the « IEX » chromatograms.

| No. | Retention time (min) | Name of the peak | Quantification of the isoforms of the FVII (in %) |
|---|---|---|---|
| Factor VII of the invention | | | |
| 1 | 26.43 | FVII 9GLA | 95 |
| 2 | 28.04 | FVII 10GLA | 5 |
| Total | | | 100 |
| FVII-rec | | | |
| 1 | 26.58 | FVII-rec 9GLA | 76 |
| 2 | 28.23 | FVII-rec 10GLA | 24 |
| Total | | | 100 |

Caption: « FVII 9GLA » means factor VII for which the majority isoforms have γ-carboxylation on nine residues of glutamic acid, « FVII 10GLA » means factor VII for which the majority isoforms have γ-carboxylation on 10 residues of glutamic acid.

From the results shown in Table 5, the result is that the majority isoforms of the factor VII of the invention are forms having 9 γ-carboxylations (95%). Among the isoforms of FVII-rec, 76% of the isoforms have 9 γ-carboxylations and 24% of the isoforms have 10 γ-carboxylations.

Example 6: Study of the Isoelectric Point

The separation of the different isoforms of the factor VII according to their isoelectric point was achieved by isoelectric focusing «IEF». The electrophoretic migration is carried out on a gel Focusgel 3-10 (Serva).

The quality of the factor VII batches is evaluated by analyzing the different isoforms of the product after migration on a gel with a pH gradient 3-10 under native (non-reducing and non-denaturating) conditions, according to the general analysis procedure by IEF on a Multiphor system (GE Healthcare).

The IEF analysis is carried out on Focusgel 3-10 without any SERVA well. The concentration is estimated by measurement of OD at 280 nm ($\varepsilon$=1.36 $g^{-1}$·L·$cm^{-1}$) after desalting the product on an ultracentrifugation membrane (cut-off threshold: 10 kDa).

The migration occurs according to the following electric parameters (gradient mode):

| Step | Voltage (V) | Amperes (mA) | Power (W) | Time (min) |
|---|---|---|---|---|
| 1 | 375 | 35 | 20 | 29 |
| 2 | 500 | 30 | 20 | 1 |
| 3 | 750 | 30 | 25 | 99 |
| 4 | 2000 | 20 | 35 | 1 |
| 5 | 2000 | 20 | 35 | 20 |

The proteins are revealed by staining with Coomassie Blue CCB-G250.

The determination of the pI of the isoforms is accomplished after digitization of the gel and analysis by the Quantity One (Bio-Rad) software package.

The «IEF» profiles of the batch of factor VII of the invention and of the FVII-rec are shown in FIG. 4.

The determination of the pI of the bands is accomplished with a standard for which the pIs are comprised between 5.20 and 8.15. The isoelectric point of the factor VII of the invention is comprised between 6.1 and 7.3. The profile of the isoforms of the factor VII of the invention includes two major bands comprised between 6.6 and 7.0 as well as a more acid trace at pI 6.1 and a more basic trace at pI 7.3. Both main isoforms represent about 60% of the totality of the factors VII of the composition.

The isoelectric point of the factor VII-rec is comprised between 5.5 and 7.5. The profile of the isoforms of the factor VII-rec of the invention includes two major bands comprised between 6.4 and 6.8 as well as more acid traces comprised between 5.5 and 6.4 and more basic traces between 6.8 and 7.5. Both main isoforms represent about 45% of the factors VII of the composition of the FVII-rec.

Therefore, the result of this is that the isoelectric point of the factor VII of the invention is substantially more homogeneous than the one observed for FVII-rec.

Example 7: Activity of the Factor VII of the Invention

The dosage of the FVII is carried out by an amidolytic method (FVII:am) which measures its biological activity, i.e. the factor VIIa/tissue factor complex capability of activating the factor X in the presence of calcium ions and of phospholipids.

This method is a chromogenic dosage with kinetics in two steps: activation of FX under the action of FVIIa, in a reaction mixture containing thromboplastin and calcium; and then enzymatic cleaving of a specific chromogenic substrate by FXa which releases a chromophore which may be quantified by spectrophotometry.

The kinetics readout is accomplished at 405 nm against a reference filter at 490 nm.

The thereby obtained results are shown in Table 6.

TABLE 8

Dosage of the specific activity of the factor VII of the invention

| Samples | Amidolytic activity (IU/ml) | FVII-Ag: Protein level (mg/ml) |
|---|---|---|
| FVII of the invention (batch 1) | 3307 | 0.9 |
| FVII of the invention (batch 2) | 3377 | 1.1 |
| FVII of the invention (batch 3) | 3067 | 1.0 |

The amidolytic activity of factor VII of the invention is comprised between 3,067 IU/ml and 3,377 IU/ml.

The invention claimed is:

1. A method of making a composition comprising factor VII molecules having a substantially homogeneous isoelectric point, said method comprising:
    (a) inserting a DNA sequence comprising a gene encoding for factor VII in an embryonic non-human mammal, said gene being under the transcriptional control of a beta-casein promoter,
    (b) transferring the embryos obtained in step a) into an oviduct of a female non-human mammal so that it develops into an adult mammal,
    (c) inducing lactation in the adult non-human mammal obtained in step b) of the female type or in a female descendant of the non-human mammal wherein the gene and the promoter are present in its genome,
    (d) collecting milk of the lactating non-human mammal, and
    wherein the female non-human mammal is a rabbit,
    wherein among all N-glycan forms of the factor VII molecules, between 70% and 80% of the N-glycan forms are monocharged and between 15% and 25% of the N-glycan forms are bicharged,
    wherein at least 80% of the factor VII molecules have γcarboxylation on 9 residues of glutamic acid, and
    wherein the factor VII originated from transgenic rabbits produced by microinjection of an expression vector comprising a beta-globin insulating sequence from chicken, a control region of goat beta-casein at 5', an optimized cDNA sequence for expression in mammal cells coding for human FVII, a non-translated region of beta-casein at 3'
    (e) purifying factor VII present in the collected milk.

2. A method for formulating a composition of activated factor VII, said method comprising mixing a composition of activated factor VII with a buffer solution, adjusting the pH if required, filtering, and then drying if necessary to obtain a solid form,
    wherein the composition of activated factor VII comprises factor VII molecules, wherein among all N-glycan forms of the factor VII molecules, between 70% and 80% of the N-glycan forms are monocharged and between 15% and 25% of the N-glycan forms are bicharged,
    wherein at least 80% of the factor VII molecules have γcarboxylation on 9 residues of glutamic acid, and
    wherein the factor VII originated from transgenic rabbits produced by microinjection of an expression vector comprising a beta-globin insulating sequence from chicken, a control region of goat beta-casein at 5', an optimized cDNA sequence for expression in mammal cells coding for human FVII, and a non-translated region of beta-casein at 3'.

3. The method of claim 2, wherein the steps for mixing the composition of the activated factor VII with a buffer solution is applied in gel filtration chromatography.

4. The method of claim 2, further comprising freeze drying the formulated factor VII composition.

5. The method according to claim 2, wherein the buffer solution comprises one or more of:
    a) a salt;
    b) an amino acid, a hydrophilic amino acid salt, or a hydrophobic amino acid salt.

6. The method according to claim 5, wherein the salt is a citrate salt.

7. The method according to claim 6, wherein the citrate salt is trisodium citrate.

8. The method according to claim 5, wherein the hydrophilic amino acid salt is arginine hydrochloride and/or lysine hydrochloride.

9. The method according to claim 5, wherein the amino acid is a hydrophobic amino acid.

10. The method according to claim 9, wherein the hydrophobic amino acid is isoleucine and/or glycine.

* * * * *